United States Patent [19]

Sluyter

[11] Patent Number: 4,805,027

[45] Date of Patent: Feb. 14, 1989

[54] INTEGRATED BEAM SPLITTER VIDEO CAMERA AND METHOD

[75] Inventor: Erik Sluyter, Santa Barbara, Calif.

[73] Assignee: Circon Corporation, Santa Barbara, Calif.

[21] Appl. No.: 64,855

[22] Filed: Jun. 18, 1987

[51] Int. Cl.⁴ .................................................. A61B 1/04
[52] U.S. Cl. ...................................... 358/225; 358/98; 354/62; 128/6; 128/634
[58] Field of Search ...................... 354/62; 358/225, 98; 128/634, 6

[56] References Cited

U.S. PATENT DOCUMENTS

| 4,192,591 | 3/1980 | Yobaccio | 354/62 |
| 4,369,767 | 1/1983 | Shishido | 354/62 |
| 4,439,030 | 3/1984 | Veda | 354/62 |
| 4,682,586 | 7/1987 | Matsuo | 354/62 |

FOREIGN PATENT DOCUMENTS

| 0087033 | 8/1983 | European Pat. Off. | 358/98 |
| 0211134 | 12/1983 | Japan | 358/98 |

Primary Examiner—Russell E. Adams
Attorney, Agent, or Firm—Daniel J. Meaney, Jr.

[57] ABSTRACT

An integrated beam splitter video camera for processing an optical image from an endoscope is shown. The integrated beam splitter video camera includes a housing having a central area which extends therethrough, an optical aperture for passing an optical image to be processed from an endoscope along a predetermined path into the central area of the housing, and a viewing opening for viewing the optical image. A beam splitting surface, located along the predetermined path and within the central area of the housing, receives the optical image and, with a minimum absorption loss in the visible spectrum, transmits a nominal portion of the optical image along a first optical path and reflects the remaining substantial portion of the optical image along a second optical path which is at a selected angle to the first optical path. A viewing optical system is positioned within the central area of the housing and along the first optical path to intercept the nominal portion of the optical image for forming a viewable image of the optical image which is viewable through the viewing opening. An optical image processing system, located within the housing, is positioned relative to the second optical path to receive and process the remaining substantial portion of the optical image. The optical processing system includes a sensor-converter for producing video signals representing the optical image. A method for processing the optical image is also shown.

26 Claims, 2 Drawing Sheets

INTEGRATED BEAM SPLITTER VIDEO CAMERA AND METHOD

1. Field of the Invention

This invention relates to an integrated video camera and beam splitter assembly, adapted for use with an optical device which produces an otical image wherein the video camera produces video signals which are representative of an optical image while the optical system concurrently produces a viewable image of the optical iamge. More particularly, this invention relates to an integrated beam splitter video camera having a compact housing which is adapted to be operatively coupled to an endoscope which produces an optical image. The optical image produced by the endoscope is received by the integrated beam splitter video camera and is processed to concurrently produce a viewable optical image and preprocessed video signals representative of the the received optical image. The preprocessed video signals produced by the integrated beam splitter video camera are amplified and transmitted via a cable to a remote video processing output circuit.

2. Description of the Prior Art

The use of video camers in the medical, surgical and industrial fields is well known in the art. Specifically, it is well known in the art to couple a focusable video camera to an optical imaging producing device, such as, for example, to a medical endoscope, for producing video images. Typical of such focusable video cameras for use with endoscopes are those disclosed in U.S. Pat. Nos. 4,600,938; 4,600,939; 4,600,940 and 4,639,772, all having a common Assignee with this invention, that common Assignee being Circon Corporation of Santa Barbara, California.

Each of the focusable video cameras disclosed in U.S. Pat. Nos. 4,600,938; 4,600,939; 4,600,940 and 4,639,772 are adapted to be operatively attached to standard medical endoscopes which are designed to produce an optical image which is directly viewable by a user through a viewing port. During surgery, the surgeon views the optical image produced by the endoscope through a viewing port which is typically integral with the endoscope. In order to simultaneously produce both a viewable image of the optical image and a video image thereof, a video camera is operatively attached to separate a beam splitter, white beam splitter is, generally, operatively attached between the viewing port of the endoscope and the video camera. The beam splitter typically transmits or reflects, as the case may be, about 50% of the optical image along a first optical path to a viewing lens system which transmits the so formed viewable optical image to a viewing opening so that the surgeon can to view the same.

Concurrently, the remaining 50% of the optical image is transmitted or reflected, as the case may be, by the beam splitter along a second optical path in the same plane, a portion of which is at a selected angle to the first optical path, to a video camera. The video camera includes a lens system that is moveable to adjust for differences in optical images produced by different endoscopes. The lens system adjusts the optical image as required to place the same the focal length of the video camera.

The focusable video camers disclosed in U.S. Pat. Nos. 4,600,938; 4,600,939; 4,600,940 and 4,639,772 are adapted to be soakable in disinfectant solutions or to be sterilized by using an ETO sterilizing gas.

A typical medical endoscope includes an internal lens system which produces an optical image in a form that the same can be viewed from the endoscope port by the human eye. The optical image is such that it can be viewed by the human eye which typically has different characteristics than that of a video camera. As such, focusing of the optical image onto the sensor-converter is required and a separate focusable lens system is used to provide that focusing capability.

It is also knonw in the art to design the endoscope to have an internal lens system to produce an optical image therefrom which is directly compatible with and at the focal length of a sensorconverter. As a result, a video camera, without a focusing means, may be directly operatively attached to the viewing port of the endoscope.

Typically, in such specially designed endoscopes, the optical image at the viewing port appears unfocused to the human eye, but the optical image is in focus to the video camera. The video camera receives the focused optical image and produces video signals representative of the optical image. The video signals are processed remotely by a video processing circuit to produce a video image on a video monitor which is the only image viewable by the user. Typical of such specially designed endoscope adapted to have a video camera directly attached thereto and which do not concurrently provide a direct viewable image for the surgeon to view are: (i) an endoscope manufactured and offered for sale by Dyonics, Inc. of Andover, Massachusetts and which is marketed as the Dyonics VideoArthoscope; and (ii) an endoscope manufactured and offered for sale by Cabot Medical of West Langhorne, Pennsylvania and which is marketed as the Cabot Medical Videoscopes.

It is also known in the art to utilize a beam splitter in combination with an automatic light shuttering control An integrated beam splitter and adjustable light intensity control adapter is disclosed in U.S. Pat. No. 4,344,667.

An automatic iris control system for a video camera using a beam splitter is disclosed in U.S. Pat. No. 4,300,167.

It is also known in the art to place an adjustable light dimming element in the imaging forming light path between a camera lens and the endoscope eye piece, and such a device is disclosed in West Germany Patent No. 2,009,642.

A rotatable adapter for use in optically coupling a viewing device with a photographic camera is disclosed in U.S. Pat. No. 4,192,591. In U.S. Pat. No. 4,192,591, a Polaroid camera is adapted to be operatively coupled to an endoscope to receive and photograph the optical image. The optical image is intercepted by a beam splitter which transmits about 50% of the optical image to a viewing opening where the same can be observed by a user. The beam splitter reflects approximately 50% of the optical image along a separate optical path to the camera, which optical path is in the same plane as the transmission optical path. The separate optical path includes a fixed lens system and a reflecting mirror which is likewise in the same plane as the transmission and reflected optical image paths. The reflecting mirror is in a housing section that is rotatable around the axis of the transmission path so as to direct the reflected light in preestablished position into a camera lens independent of the position of the rotatable housing. The reflecting mirror reflects the transmitted optical image 90° and then directs the same through a second fixed lens onto the lens of a Polaroid camera system. The Polaroid camera system includes a separate and remote electronic control device to control a separate light system to flash or flood the image with light at the time that the camera is actuated to photograph the optical image thereby insuring that sufficient light is passed through the endoscope at the time the optical image is recorded or photographed. An electromechanical shutter is is opened to photograph the image, and a light sensing circuit determines the brightness of the optical image and commands the shutter to close upon detection of a predetermined exposure value. The lens of the Polaroid camera system is a manually focused through the Polaroid camer's through-the-lens-viewing system to insure that a focused aerial image is presented to the film plane within the camera. The viewing opening in the adapter permits simultaneous viewing and photographing, or simultaneous viewing by two people.

An articulated optical coupler using a folded optical path, a lens and a plurality of reflecting mirrors to direct the optical image along a moveable optical path within an articulated arm assembly and as an input a video camera, which image does not move or rotate as the articulated arm assembly is moved is disclosed in U.S. Pat. No. 4,428,213.

SUMMARY OF THE INVENTION

The present invention relates to a new and novel integrated beam splitter video camera which is capable of processing an optical image from an optical image generating device, such as for example, an image from an endoscope used for surgery in the medical field. The integrated beam splitter video camera is capable of simultaneously producing a viewable optical image and preprocessed video signals representing the optical image. The so produced preprocessed video signals are transmitted to a remote video processing output means for further processing. The remote video processing output means may produce composite color video signals which, in turn, are applied to a standard color video monitor or color television set to produce a color video image of the optical image. The same principles are applied to produce black and white video images.

In the preferred embodiment of the present invention, the integrated beam splitter video camera is adapted for processing an optical image from a endoscope. The integrated beam splitter video camera includes a housing having means for defining a central area which extends therethrough. The housing including means for passing an optical image, to be processed, form an endoscope along a predetermined path into the central area of the housing. A differential transmission/reflecting optical image means is located along the predetermined path within the central area of the housing and receives the optical image. The differential transmission/reflecting optical image means, with a known absorption loss in the visible spectrum, transmits a nominal portion of the optical image along a first optical path and reflects the remaining substantial portion of the optical image along a second optical path, a portion of which is at a selected angle to the plane containing the first optical path. A viewing means, positioned within the central area of the housing and along the first optical path, intercepts the nominal portion of the optical image and forms a viewable image of the optical image. An optical image processing system, located within the housing, is positioned relative to the second optical path to receive and process the remaining substantial portion of the optical image. The optical image processing system including means for producing video signals representing the optical image. The differential transmission/reflecitng optical image means includes a beam splitter cube having a beam splitting surface which is coated with a material that results in an absorption loss of about 10% in the visible spectrum and which transmits about 5% to about 10% of the optical image along the first optical path and relfects about 70% to about 80% of the optical image along said second optical path. The beam splitter surface is positioned at an angle of about 45° relative to the predetermined path to intercept the optical image. In the preferred embodiment, the beam splitting surface is coated with a metal-dielectric material that results in an absorption loss of about 10% in the visible spectrum and which transmits about 8% of the optical image along the first optical path and about 72% of the optical image along said second optical path. A reflecting mirror is positioned relative to the beam splitter surface for reflecting the remaining substantial portion of the optical image along a folded optical path portion or the seocnd optical path. The second optical path is at a selected angle relative to the first optical path and includes a folded optical portion to direct the remaining substantial portion of the image onto a sensorconverter.

Certain of the prior art focusable cameras, such as those disclosed in U.S. Pat. Nos. 4,600,938; 4,600,939; 4,600,940 and 5,639,772, require the use of a separate beam splitter optical element in order to provide a viewable optical image and to provide a second split image for the video camera to process simultaneously to produce the video signals. The beam splitter is a separate optical element, and typically requires separate sterilization in order to be closed in a surgical application with a video camera.

One significant disadvantage of the prior art devices using a separate beam splitter component is that the beam splitter itself has two adapters, one to operatively connect the beam splitter to the endoscope, and a second adapter to operatively connect the video camera to the beam splitter. Further the prior art video cameras have many more mechanical parts than that of the present invention.

As a result of the mechanical structure of the prior devices, such devices have more mechanical parts, and are, therefore, heavier in weight than the beam splitter camera of the current invention. Further, due to the large number of mechanical parts, the prior art devices have less reliability and experience, to a certain degree, certain mechanical failures because of the numerous components.

Certain of the prior art systems, such as those disclosed in U.S. Pat. Nos. 4,344,667, 4,300,167. and West Germany Pat. No. 2,009,642 include means for monitoring a portion of the optical image into with a light responsive or light sensitive control means to insure that the optical image has a minimum intensity for the video camera or photograph takin device.

Certain of the prior art endoscopes, such as the Dyonics VideoArthoscope and Cabot Medical Videscopes, have an internal lens system which produces an optical image therefrom which is focused directly on a sensor-converter without a focusing means. In such specially designed endoscopes, the optical image at the viewing port, appears unfocused to the human eye, and a separate viewable image is not available to a user. The video camera receives the focused optical image and produces video signals representative of the optical image which must be remotely processed by a video processing circuit to produce a video image on a video monitor which is the only image viewable by the user and the only viewable image produced from the endoscope. During surgery using the specially designed endoscopes, the surgeon does not have the capability of looking at two simultaneously generated images, and must rely on the video image produced on a video monitor.

The rotatable adapter for use in optically coupling a viewing device with a photographic camera, disclosed in U.S. Pat. No. 4,192,591, utilizes a beam splitter. The beam splitter appears to transmit about 50% of the optical image to a viewing opening, where the same can be observed by a user, and about 50% of the optical image appears to be reflected along a separate optical path, which is in the same plane as the transmission optical path, through a fixed lens system, onto a reflecting mirror, through a second fixed lens onto the lens of a Polaroid camera system. A separate and remote electronic control device is required to control a separate light system to insure that sufficient light is passed through the endoscope at the time the lens is actuated to record the optical image. An electromechanical shutter is opened to photograph the image, and a light sensing circuit determines the brightness of the optical image and commands the shutter to close upon detection of a predetermined exposure value. This adapter, consisting of a number of separate components, is bulky and requires the use of a controlled light source to insure that the optical image focused on the film plane, has sufficient intensity to image the film.

The articulated optical coupler, as disclosed in U.S. Pat. No. 4,248,213, using a folded optical path, a lens and a plurality of reflecting mirrors to direct the optical image along a moveable optical path within an articulated arm assembly to direct an optical image onto a television camera. This assembly does not include means for forming a separate viewable image, and the arm assembly is bulky, making it difficult to use during surgery.

Another disadvantage associated with the prior art devices is that the beam splitter is a separate optical component and is adapted to be mounted intermediate the viewing port of an endoscope and a video camera. In such assembly when the same is used in a medical or surgical application, the beam splitter must be sterilized separately from the video camera. After sterilization, it is not uncommon for the beam splitter, when joined to the video camera, to have some slight amount of moisture trapped therein. During use, the beam splitter and the video camera are operatively attached and the assembly is then attached to the viewing port of the endoscope. It is not uncommon for traces of fluid captured or remaining on the beam splitter camera interface or on the beam splitter/endoscope interface to vaporize and fog the lens system which disrupts the optical image as the same passes from the endoscope to the beam splitter and from the beam splitter to the video camera. Any such fogging results in a diminishment of the light intensity, blurring of the optical image or a reduction of the intensity level of the optical image ultimately passed to the video camera for processing.

One advatnage of the present invention is that the housing, the beam splitter, the sensor-converter, pre-processing video electronics and optical system are located in the interior of and integral with the entire housing such that the integrated beam splitter video camera is one compact, light weight sealed unit.

Another advantage of the present invention is that the housing completely encloses the internal optical paths, the beam splitter surfaces, all of the optical processing systems and sensorconverter. The housing includes a soakable enclosure means which surrounds the entire housing, making the same fluid tight.

Another advantage of the present invention is that the housing containing the beam splitter, the optical system and a sensorconverter means is a soakable unit such that the entire assembly, including the beam splitter interior to the housing, can be placed into and be soakable in disinfectant solutions or, in the alternative, can be sterilized by using an ETO sterilizing gas.

Another advantage of the present invention is that integral beam splitting video camera includes both the beam splitter and the sensor-converter means in a single housing and, when the same is sterilized in a disinfectant solution, none of the solution can be interposed onto the surface of the beam splitter or between the beam splitter surface and the video camera in that the same are enclosed in a soakable housing. As a result of the integrated beam splitter video camera being enclosed in a sealed housing, the fogging of the optical path between the beam splitter surface and the surface of the sensor-converter means, which functions as a video camera, is eliminated. This enables an optical image to be transmitted and reflected by the beam splitting surface without interference from fogging and the like such that a substantial portion of the optical image is transmitted, unobstructed, along an optical path to the sensor-converter means.

Another advantage of the present invention is that the video camera can utilize a charge couple device, an advanced solid state sensor, and beam splitter, in combination, in a unitary housing unit.

Another advantage of the present invention is that the number of adapters required to operatively connect the beam splitter video camera of the present invention to an endoscope is reduced to one as compared to two as required by the prior art devices. Further, the number of elements in the beam splitter video camera of the present invention is reduced in number resulting in a lesser number of overall mechanical components relative to the prior art devices. Thus, the beam splitter video camera of the present invention has lower weight, has fewer mechanical components resulting in greater reliability and fewer mechanical failures.

Another advantage of the present invention is that a substantial portion of the optical image is transmitted by the beam splitter surface along an optical path to a sensor-converter means used as the video camera. A nominal portion of the optical image is transmitted, along a separate optical path, which image can be utilized for a plurality of viewing purposes, such as for example, to form a viewable image of the optical image or for photographing the same.

A further advantage of the present invention is that a raised eye piece can be sealingly affixed to a viewing opening in the housing so that a viewable image and optical image can be observed through the eye piece by a surgeon during surgery.

Another advantage of the present invention is that the video signals produced the integrated beam splitter camera permits concurrent viewing of a representation of the optical image on a video monitor screen.

Another advantage of the present invention is that the integrated beam splitter video camera can be attached to standard endoscope and includes means for focusing the lens system to compensate for any variance between endoscope and in order to focus a sharp optical image ontok, and which cna be faithfully reproduced by, the sensor-converter means.

Another advantage of the present invention is that the preprocessed video signals can be applied to a video output circuit. The video output circuit may be a video signal processing means which produces a composite video signal having vertical blanking signals and horizontal synchronizing signals so that the video image can be viewed on a monitor screen or be recorded on a video cassette recorder or other appropriate video signal recording system.

Another advantage of the present invention is that a vented adapter can be utilized for operatively removably coupling the integrated beam splitter video camera to the viewing port of an endoscope. The vented adapter permits air to flow through the adapter to flush away any moisture, dust particles or the like which would fog or otherwise blur the image from the viewing port at the end of the endoscope.

Another advantage of the present invention is the cable utilized for transmitting the preprocessed video signals from the integrated beam splitter video camera to a remote video output circuit includes a connecting means which permits the cable to be quickly and easily replaced without disassembly of the housing.

Another advantage of the present invention is that the integrated beam splitter video camera has wide utility in the medical field such as surgery, or the industrial field, such as for boroscopes.

BRIEF DESCRIPTION OF THE DRAWING

These and other advantages of the invention will be readily apparent when considered in light of the detailed description hereinafter of the preferred embodiment and when considered in light of the drawing set forht herein which includes Figures.

DESCRIPTION OF THE PREFERRED EMBODIMENT

Figures 1, 2:
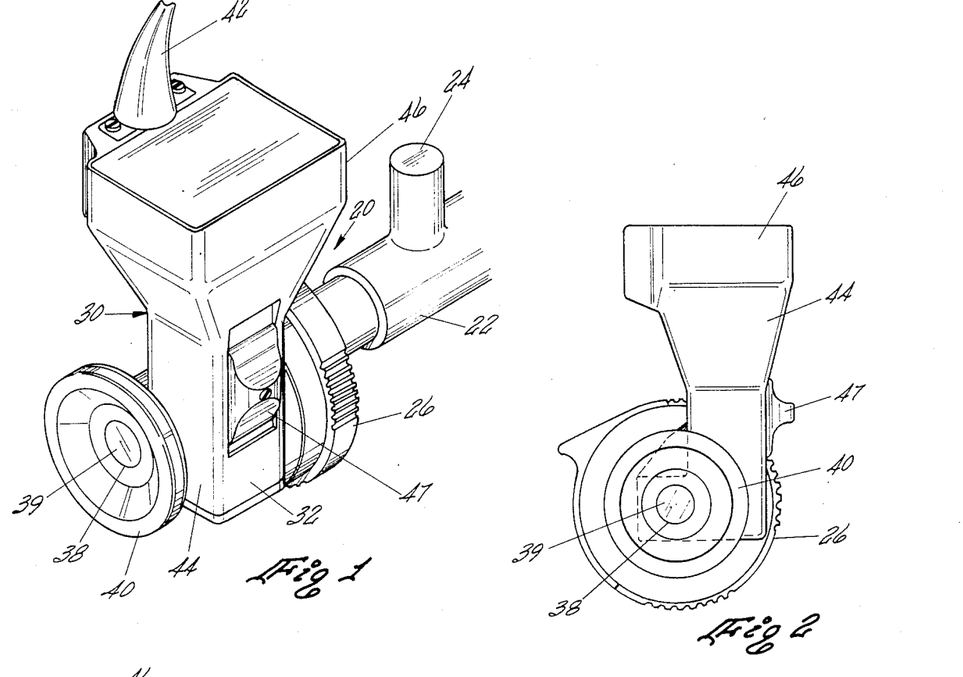
FIG. 1 is a top, front and left side propspective view of an integrated beam splitter video camera of the present invention, having a raised eye piece and a vented adapter which is adapted to be operatively connected to an endoscope.
FIG. 2 is a left side plan view of an integrated beam splitter video camera.

FIG. 1 illustrates, by means of a perspective view, an integrated beam splitter video camera shown generally by arrow 20. The beam splitter video camera is used for processing of an optical image from an optical viewing device to produce a video signal representative of the optical image. In the preferred embodiment, the integrated beam splitter video camera 20 is adapted to be optically connected to an endoscope 22 which includes an input means 24 for applying light to the endoscope to produce an optical image at the distal end thereof as is well known in the art. The integrated beam splitter video camera 20 is optically connected to the endoscope 22 by means of a vented adapter shown generally as 26. The vented adapter is fabricated such that air is capable of passing therethrough to flush, from the opening between the optical aperture located in the integrated video camera 20 and endoscope 22, any moisture, dust particles and the like located therebetween.

Figure 6:
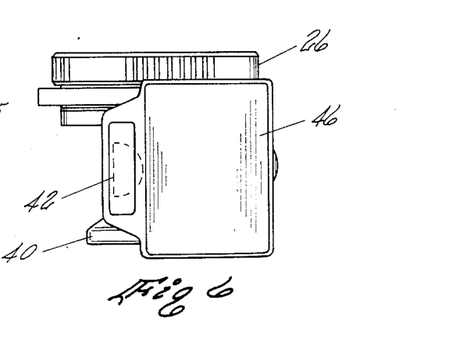
FIG. 6 is a top plan view of the integrated beam splitter video camera of FIG. 1.

The integrated beam splitter video camera 20 includes a housing 30 which includes means for defining a central area which extends therethrough. The housing 30 includes means for defining a front end portion 32 and includes means for defining a cavity having two ends. This cavity extends along a first optical path and includes an optical aperture, shown as element 34 in FIG. 6, which is adapted to permit the optical image, produced by the endoscope 22, to be passed into the housing 30 and specifically to the front end portion 32 thereof. The aperture opening 34 is sealed with a transparent glass window 35 to faithfully pass the image as shown in FIG. 7.

The front end portion of 32 also includes means for defining at the other opposite end of the cavity formed within front end portion 32, a viewing opening 38 having a glass window. A means, positioned along the optical path such as raised eyepiece 40, is adapted to intercept a nominal portion the optical image passing along the optical path through the cavity of the front end portion 32 and for forming a viewable image of the optical image. The viewing opening 38 is sealed with a transparent glass window 39 to faithfully pass the image as shown in FIG. 7.

The housing 20 includes the elongated central portion 44 which has a hollowed out central area and a rearward portion 46. The elongated central portion 44 and the rearward portion 46 define a hollowed-out central area which is substantially perpendicular to and which communicates with the cavity of the front end portion of 32. The elongated central portion 44 encloses a second optical path and the hollowed central area of the remote end 46 encloses the sensor-converter, which is shown as element 70 in FIG. 7.

Figures 7, 8:
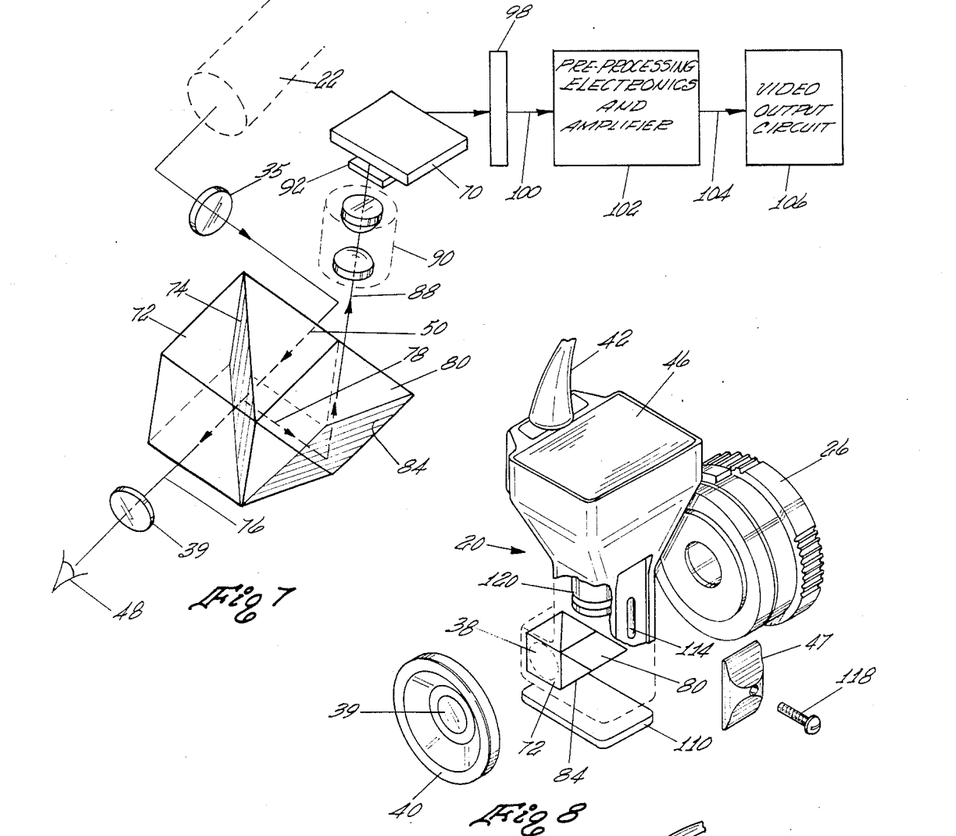
FIG. 7 is a pictorial representation of a beam splitter cube having a beam splitting surface, a right angle prism having a reflective mirror for receiving an optical image and for transmitting a nominal part of the image along a viewing path and to reflect the remaining substantial portion of the optical image along an optical path through an objective lens focusing system and onto a sensor-converter to produce video signals which are subsequently applied as preprocessing video signals to a video output circuit.
FIG. 8 is a partial perspective exploded view of an integrated beam splitter video camera showing the relationship between the front end portion of the housing an assembly comprising the beam splitter and prism having a reflection mirror, which assembly is located in the front end portion of the housing.

The elongated central portion 44 of housing 20 further encloses a portion of the optical imaging processing system which is positioned relative to the optical path as is illustrated in FIG. 7. The optical imaging processing system specifically includes a lens system, which is positioned in the elongated central portion 44, which functions to focus the optical image onto a sensor-converter located in the rearward portion 46 of the housing 20.

A cable 42 is used to carry the preprocessed video signals to an external video output circuit as shown in FIG. 7.

Figures 3, 5:
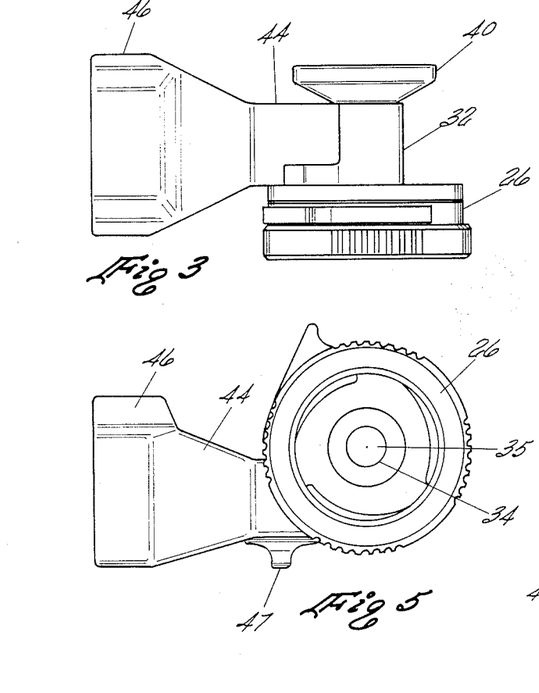
FIG. 3 is a back elevational plan view of the integrated beam splitter video camera of FIG. 1.
FIG. 5 is a right side elevational view of the integrated beam splitter video camera of FIG. 1.
Figure 4:
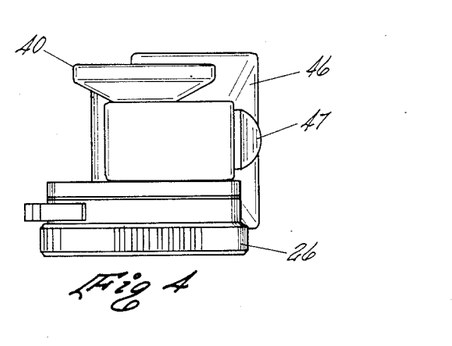
FIG. 4 is a bottom plan view of the integrated video camera of FIG. 1.
Figure 9:
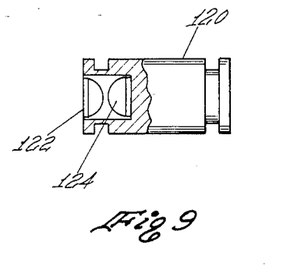
FIG. 9 is a front plan view, partially in cross section, of a cylindrical lens housing which includes a pair of spaced objective lens which are interposed between the reflecting surface of the prism and the surface of a sensor-converter means for focusing the optical image onto the sensor-converter means.

A slideable boss 47 is used to move a cylindrical lens housing, shown in greater detail in FIG. 5, 8 and 9, in order to focus the optical image on the sensor-converter 70 shown in FIG. 7.

FIGS. 2, 3, 4, 5 and 6 show the relative position of the front end portion 32 relative to the view opening 38, the eye piece 40, the optical aperture 34 and the vented adapter 26. As illustrated in FIG. 8, transparent, fluid tight windows are provided for the view openign 38 and the optical aperture 34.

The size and shape of the integral video camera is very compact, say in the order of 2 inches long and 1.5 inches wide, such that the same can easily be operatively attached to an endoscope by the vented adapter 26. The housing is sufficiently compact so as not to interfere with a surgeon's hand placement while enabling the surgeon to view the optical image during surgery through the eye piece 40, which image appears at viewing aperture 38. The image which passes to the viewing aperture 38 is generally referred to herein as the image passing along the first optical axis. A second image is directed through the elongated central section 44 of housing 30 through an optical processing system, and then is generally referred to herein as the seocnd optical axis.

The entire design of the housing the 30, including the optical aperture 34 and window 35, illustrated in FIG. 5, and the viewing aperture 38 and window 39 illustrated in FIG. 2, are fluid tight so that the entire housing is essentially a soakable enclosure means. The soakable housing surrounds all of the internal optical paths, the solid state imaging means, which is in the form of a sensorconverter, and a video signal preprocessing means which will be described in greater detail hereinafter. The soakable enclousre means can be sterilized in a standard fluid sterilizing solution, or in the alternative, can be sterilized by the use of an ETO gas sterilization procedure.

In this manner, none of the interior elements, including the optical paths, the solid state imaging means or the video signal preprocessing means are exposed to any of the sterilizing fluids, gas or other the like, thereby eliminating the possibility of fogging, contamination or otherlike, which may arise if those components were directly subjected to a sterilizing fluid or gas.

Referring now to FIG. 7, the pictorial representation depicts an optical image receiving means which is located along a predetermined path 50, located interiorly of the housing 30. Specifically, a differential optical image transmitting and reflecting means, such as a beam splitting surface 74, is located along the predetermined path 50, located in the front end portion 32 of housing 30, the differential optical image transmitting and reflecting means receives the optical image, which has been passed thereto from the endoscope 22 through the image aperture 34 (shown in FIG. 5), window 35, and along the predetermined path 50. The differential optical image transmitting and reflecting means 74 functions in a manner similar to that of a beam splitter, except, however, that the portion of the image transmitted along one optical axis and the portion of the image reflected along a second optical axis differ significantly in video camera applications over standard beam splitters ratio of transmission and reflection. Specifically, a beam splitter cube 72 includes a beam splitter surface 74 which functions in the following manner. The optical image is passed along the predetermined path 50 and is intercepted by the beam splitting surface 74. Typically, the beam splitter surface 72 in conjunction with the differential transmission/reflecting surface thereof, absorbs a predetermined portion of the optical image with a known absorption loss in the visible spectrum is known. It is envisioned that materials may be used that have a lower absorption loss. Typically, the transmission/reflecting surface is coated with a metal dielectric material that results in the absorption of about 10% of the visible spectrum and the remaining portion of the image is transmitted or reflected depending upon the coating characteristics of the surface 74. In the beam splitter surface illustrated in FIG. 7, the optical image, which is passed along the predetermined path 50, is intercepted by the differential optical image transmission reflecting surface 74 positioned at a selected angle thereto. A nominal portion of the optical image is diverted along a first optical path 76 and the remaining substantial portion of the optical image is reflected along a second optical path 78.

In the preferred embodiment, approximately 8% to about 10% of the optical image is transmitted by the differential transmission/reflecting surface 74 along the first optical path 76. The beam splitter surface 74 reflects about 80% to about 90% of the optical image along the second optical path 78. In the preferred embodiment the beam splitter surface 74 is positioned at an angle of about 45° relative to the predetermined path 50 so as to intercept the optical image path which extends from the beam splitter surface 74 to the viewing aperture 38.

In one design of the preferred embodiment, the differential transmission/reflecting surface 74 of the beam splitter cube 72 is coated with a metalic-dielectric material, having an absorption loss of about 10% in the visible spectrum. This resulted in the transmission along the first optical axis 76 of about 8% of the optical image and the reflected portion of that image along the second optical axis being about 72%. The difference between the 100% beginning received optical image less: (i) the transmitted portion of about 8%, and (ii) the reflected portion of about 72% appears to be the light and/or absorption loss.

The image transmitted along the first optical axis 76 passes through the viewing opening 38 (shown in FIG. 2) and window 39 the is a viewable image because it is received directly from the endoscope 22. The eye of a user, shown generally as 48, views the viewable image through the viewing opening 38 in eye piece 40 shown in FIG. 1 and FIG. 2. Although only a nominal portion of the optical image, say in the order of about 8% to about 10%, is available for viewing at the viewing aperture 38, the human eye is able to adjust its viewing characteristics to receive and view an image even though the intensity level thereof is would be 10%.

Referring again to the beam splitter reflecting surface 74, the reflected portion of the optical image, which is the remaining substantial portion of the optical image originally passed along the predetermined path 50, is reflected onto a prism 80 having a 100% reflecting surface 84, which reflection surface functions as a reflecting mirror. The reflecting surface 84 is positioned to intercept the optical image passing along the second optical path 78 and to reflect the same along a second portion 88 of the second optical path defining a folded portion of the second optical path at an approximately 90° degree angle. The optical path shown by dashed lines 78 and 88 are referred to herein collectively as the second optical path. As such, the second optical path is a folded optical path, having a portion of which is at a selected angle to the first optical path. The optical image represented by dashed line 88 is passed through a pair of objective lenses, 90 located in an adjusted cylindrical lens housing 120 and onto a surface of a sensor-converter 70.

A laminated filter 92 is provided between the objective lens 90 and the sensor-converter 70. The filter 92 performs the function of a spatial frequency filter for the optical image, as a color correction filter and as an infrared blocking filter.

The sensor-converter 70 is responsive to the optical image having an intensity above a threshold intensity level in order to produce video signals having an acceptable signal-to-noise ratio. The sensor-converter 70 requires that the optical image have a minimum threshold level such as, for example, in the range of about 5 lux to about 15 lux with the preferred embodiment having about 50 lux intensity which is significantly above the minimum, for the sensor-converter to produce unprocessed video signals containing meaningful data representing the optical image. The sensorconverter 70 is positioned to receive the optical image, passed along the second optical path, and convert the same to unprocessed video signals, which unprocessed video signals are represented by arrow 96.

In the preferred embodiment, the beams plitter cube 72 is formed of optical glass, glass type BK 7, having an $N_D$ characteristic of approximately 1.517, a V characteristic of 64.5 and grade B glass.

The beam splitter reflecting surface is polished with a fine ground surface having a flatness of approximately 4 fringes. The beam splitter is coated with a metal-dielectric hybrid material to establish the 80° reflected, 10° transmissive and 10° absorption characteristics. The cube is formed of two right angle prisms joined together, at the treated surface, using a Norland optical cement. The reflecting surface is located on the appropriate reflecting surface of a right angle prism and is coated with a material to obtain as close to 100% reflection. One material used for the mirror coating was silver having a layer of black lacquer over the back thereof. The face of the beam splitter cube receiving the optical image and the sides of the right angle prisms may be coated with black lacquer for light containing purposes.

The plating of a beam splitter surface on prisms and assembling the same to form a cube is well known in the art. The treatment and preparation of such beam splitter surfaces are enclosed in a reference manual known as Melles Griot, under the category of Plate-Type Beam Splitter, set forth at page 198 thereof.

In the preferred embodiment, the beam splitter cube has 10 mm. sides, the angle of incidence of the differential transmission/reflecting surface is about 45°, the thickness of the coated surface is approximately 1 mm. The reflecting surface is coated with a 0° Hebbar coating.

The objective lenses 90 are formed of a pair of convex lenses which have a combined focal length of approximately 16 mm. to approximately 55 mm. In the preferred embodiment, the combined focal length is approximately 27.5 mm. The position of the objective lens 90 relative to the surface of the sensor-converter 70 can be adjusted linearly along the optical axis to focus the image on the sensor-converter 70. The lens system 90 focuses the optical image on the surface of the sensor-converter 70 at an intensity level which is at least equal to the threshold intensity level of the sensor-converter as described hereinbefore. Sensorconverter circuitry means 98 causes the sensor-converter 70 to scan the sensor-converter surface to generate unprocessed video signals from the sensor-converter surface 70 representative of the optical image. The output from the sensor-converter circuitry 98 are unprocessed video signals represented by arrow 100.

Video signal preprocessing circuit means 102, which include a video signal driving means and amplifying means, is located within the housing 20 at any desired location which does not intercept the optical images passing along the first and second optical paths. In the preferred embodiment, the video signal preprocessing unit 102 is located at the remote end 46 of the housing 20. In the preferred position the video signal preprocessing circuit means 102 is remote from the second optical path 78 and its fold optional path portion 88 so as to avoid intercepting same. The video signal preprocessing electronics is included in the circuit means shown generally as 102. Unprocessed video signals, represented by arrow 100, are received by the video signal preprocessing circuitry means 102 from the sensor-converter control circuitry 96 and the circuitry means 102 and performs the function of preprocessing the unprocessed video signals and amplifying the same to a level that the preprocessed video signals can be transmitted over or driven over a cable connecting means, shown generally as 104, to a remote video output circuit shown generally as box 106. The remote video output circuit 106 may be a processing unit that generates composite video signals from the preprocessed video signals which are, in turn, applied to a video monitor, a video cassette recorder apparatus or the like.

The pictorial drawing of FIG. 7 discloses a method for concurrently producing a viewable image through a viewing aperture 38 and for producing video signals which are used to produce an image on a video monitor. As illustrated in FIG. 7, the method comprises a step of passing an optical image from an endoscope 24, along a predetermined path 50 to the housing 20. The housing 20 includes means for defining a central area which extends therethrough as depicted in FIGS. 1 through 6 thereof. Within the elongated central area of the housing 20, the step of receiving the optical image with a differential optical iamge transmitting/receiving means, which preferably is a beam splitting surface 74, located along the predetermined path 50 is shown. The beam splitting surface 74 transmits and reflects the optical image along two separate optical paths with a known absorption loss in the visible spectrum. Specifically this step comprises transmitting a nominal portion of the optical image along a first optical path 76 and reflecting the remaining substantial portion of teh optical image along a second optical path 78 having a portion of which is at a selected angle to a common plane including a portion of the firs toptical axis and a portion of the second optical axis. The selected angle between the firs toptical path and the second optical path could also be achieved by reflecting or otherise folding or changing the direction of the first optical path to the second optical path.

The next step comprises receiving and processing, with an optical image processing system which includes a sensor-converter 70, preprocessing electronics 102 and the means for applying the preprocessed amplified video signals depicted by arrow 104, to a video output circuit 106, all of which are located within the housing. The optical image processing system produces video signals representing the optical image and electrical output signals from the integrated beam splitter video camera.

Also, the method may include the step of intercepting the nominal portion of the optical image passing along the first optical path 76 for forming a viewable image of the optical iamge at a view aperture, such as viewing aperture 38.

FIG. 8 shows, by means of an exploded partially perspective view, a portion of which has dashed lines for part of the components, the relationsyhip between the housing 20, the elongated central portion 44 and the front end portion 32. The front end portion 32 defines a cavity which is adapted to receive the beam splitter cube 72, having the beam splitter surface 74 and the right angle optical prism 80. The right angle optical prism 80 includes the reflecting mirror 84 which is positioned relative to the beam splitter surface 74 to receive the image passing along a second optical axis and reflecting the same 90° so as to direct the optical image through the elongated central portion 44 of housing 20 onto the surface of a sensor-converter 70 (shown in FIG. 7) forming the selected angle between the two optical paths.

A viewable image is produced directly from the endoscope, passed through the vented adapter 26 through the optical aperture 34 having a sealed glass window 35 the beam splitter surface 74 of the beam splitter cube 72 located in the lowe rportion of housing 32, and then through the viewing opening 38 passing the viewable optical image through a glass window 39 sealing affixed to and which covers the viewing aperture 38.

An eye piece 40 is adapted to be threadably connected to the viewing opening 38 so that a vieable optical iamge passing therethrough can be viewed by a surgeon through the eye piece 40.

A bottom cover, shown generally as 110, is sealing attached to the front end portion 32 to seal the same so that fluid, gas and the like cannot permeate the seal and reach the interior of the housing.

In order to provide a focusing capability for the integrated video camera, the elongated central portion 44 of the housing includes a sealed slot 114 which is adapted to and operatively functions with the slideable adjusting boss 47. The adjusting boss 47 is attached to teh cylindrical lens housing 120 by a threaded fastener, shown in greater detail in FIG. 9. This provides a means for externally applying an external adjustment to the cylindrical lens housing 120 internally with the housing along the optical axis for positioning the objective lens 90 at a desired position to focus the optical image on the surface of the sensor-converter 70. A fastener 118 passing through the center opening of adjusting boss 47 and through slot 114, is used to operatively attach the adjusting boss 47 to the cylindrical lens housing. The exterior of the fastener 118 is in sealing engagement with a sealing member located within slot 114 to form a fluid tight seal.

FIG. 9 illustrates the structure of a focusable lens system which includes a cylindrical lens housing 120 having a pair of spaced, axially aligned concave objective lenses 122 and 124 mounted therein. The combined focal length of the objective lens may be in the range of approximately 16 mm. to about 55 mm, and the preferred focal length is about 27.5 mm. The fastener 188, illustrated in FIG. 8, is threaded into cylindrical the lens housing 120 and is responsive to movement of the boss member 47 to slide the objective lens 122 and 124 linearly along the optical axis and relative to the surface of the sensor-converter 70 (illustrated FIG. 7) to focus a sharp image onto the surface of the sensor-converter 70. The focusing means provides a means for adjusting the position of the optical image relative to thesurface of the sensor-converter surface and to compensate for differences that may exist in the focused optical image from various endoscopes.

Figure 10:
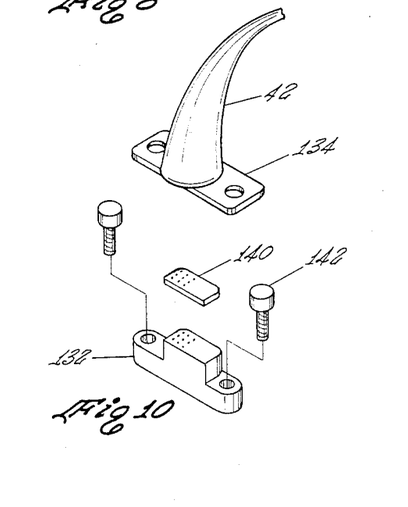
FIG. 10 is an exploded perspective view of a housing connecting means and a cable connecting means operatively connected to a cable, to permit easy replacement thereof.

In the preferred embodiment of the integrated beam splitter video camera of the present invention, a connecting cable 42 shown in FIG. 10 is utilized as part of the connecting means 104 illustrated in FIG. 7 to pass the preprocessed video signals from the integrated beam splitter video camera to a remote video output circuit, illustrated as 106 in FIG. 7. During use, the connecting cable may be damaged, cut or otherwise rendered inoperative such that it may become necessary to quickly change the same. The integrated beams plitter video camera of the present invention includes a cable disconnect means, illustrated in FIG. 10, which includes a female connecting means 132 which is affixed to and integral with the remote end portion 46 of housing 30, adapted to receive male connecting means 134 having a plurality of prewired connecting pins, used to terminate the calbe 42. The male connecting means 134 are electrically connected to electrical conductors forming the connecting calbe 42. A sealing gasket, shown generally as 140, as interposed between and functions as a sealing means between the female connecting means 132 and the male connecting means 134. The sealing mens 140 insures that sterilization fluid or sterilization gas will not penetrate into or between the assembled connecting means 132 and 134. Fastening means, shown generally as threaded screws 142, provide a means for tightly connecting the male connecting means 134, which terminates the cable 136, to the female connecting means 132 which is mounted on the housing 30 and which is electronically connected to the video signal preprocessing electronic circuits located in the interior of the housing as described hereinabove. The fastener 142 places a sufficient clamping force on the sealing means 140 to insure a fluid tight seal.

The integrated beam splitter video camera of the present invention provides a convenient, compact soakable (medical disinfectant) video camera for endoscope and has utility in the fields of urology, gastroenterology and gynecology. A charge couple device, such as CCD-III device, can be used as the sensorconverter. The beam splitting surface of the present invention directs a substantial portion, well in excess of 50% and up to about 80%, as described herein, of the optical image received from the endoscope onto the sensor-converter such that a high quality intensity optical image. By using the teachings of the present invention, a separate viewable image can still be concurrently produced for viewing the optical image for other applications, such as for example, having photographing with a camera having a high speed film with appropriate ASA ratings, which is capable of recording an optical image at a low light intensity level. In concept, dual images are concurrently produced by the integrated beam splitter video camera. A substantial portion of the optical image intensity directed to the sensor-converter to produce a high quality video image and only a nominal portion of the image is used for concurrently producing an optical image that can be viewed by a viewer or for purposes for which a viewable image is desired.

The present invention also positions the eye piece in a raised position such that the viewable optical image can easily be viewed by a surgeon during surgery.

The integrated beam splitter video camera has wide versatility and permits use of the same with a wide variety of endoscopes and enables a surgeon to receive the identical image through a remote monitor video terminal. This has application in medical teaching field or to enable another surgeon to assist in the surgery.

Also in certain industrial applications, such as for example, in inspecting the interior of jet engines and turbines, a boroscope may be used for making a visual inspection thereof as is well known in the art. The integrated beam splitter video camera can be attached to the boroscope and can be used for visually inspecting the interior of the jet engine or turbine while concurrently producing video signals which may be recorded as a permanent record of the inspection.

The integrated splitter video camera of the present invention can be attached to all type endoscopes, including those where some adjustment may be required to compensate for differences between different manufacturers of optical endoscopes. The focusable lens system of the present invention provides the means for adjusting the position of the optical image relative to the sensor-converter to produce a sharp, clear optical image, which can be processed by the sensor-converter to ultimately produce a high quality video image on a video monitor.

The vented adapter permits air to flow through the vented adapter providing a means for flushing moisture or other undesired material, i.e. dust particles and the like, from the surface of the optical endoscope thereby eliminating fogging or blurring of the optical image due to such obstructions.

Also, the detachable mcirocable assembly described in FIG. 10 hereof, provides a practical means for quickly overcoming cable problems in that the connecting cable can be easily and quickly replaced in a matter of a few minutes and with substantially no technical complications.

What is claimed is:

1. A beam splitter video camera for processing an optical iamge from a endoscope comprising
    a housing including means for defining a central area which extends therethrough, said housing icnluding means for passing an optical iamge to be processed from an endoscope along an predetermined path into the central area of said housing;
    differential transmission/reflecting means located along said predetermined path and with in the central area of said housing and, with a minimum absorption loss in the visible spectrum, for transmitting a nominal portion of said optical image along a first optical path and for reflecitng the remaining substantial portion of said optical iamge along a second optical path which includes a portion thereof which is at a selected angle to said first optical path, said differential transmission/reflecting means further including a beam splitter having a beam splitting surface which is coated with a material which, in the visible spectrum, has an absorption loss of about 10% of less;
    means positioned within said central area of said housing and along said first optical path to intercept said nominal portion of said optical image for forming a viewable image of said optical image; and
    an optical image processing system located within said housing and positioned relative to said second optical path to receive and process said remaining substantial portion of said optical image, said optical processing system including means for producing video signals representing said optical image.

2. The video camera of claim 1 wherein said coated beam splitting surface transmits about 8% to about 10% of the optical image along the first optical path and reflects about 8% to about 90% of the optical image along said second optical path, said beam splitter surface being positioned at an angle of about 45° relative to the predetermined path to intercept said optical image.

3. The video camera of claim 1 wherein said beam splitting surface which is coated with a material, which in the visible spectrum, transmits about 8% of the optical image along the first optical path and about 72% of the optical image along said second optical path.

4. The video camera of claim 1 wherein said differential transmission/reflecting means further includes
    a reflecting surface positioned relative to said beam splitter surface for reflecting the remaining substantial portion of said optical image at said selected angle relative to the first optical path.

5. The video camera of claim 4 wherein said selected angle is about 90°.

6. The video camera of claim 1 wherein said optical image processing system further comprises
    a sensor-converter which is responsive to an optical image having an intensity above a threshold intensity level, said sensor-converter being positioned to receive said optical image reflected along said second optical path and for converting the optical image to unprocessed video electric signals; and
    a lens system positioned between said sensor-converter and said means for focusing the remaining substantial portion said optical image onto said converter-sensor.

7. The video camera of claim 6 wherein the optical image processing means further comprising
    video signal preprocessing circuits means located within said housing and remote from the first optical path and the second optical path so as to avoid intercepting the same second video signal preprocessing circuit means being operatively connected to the sensor-converter means for receiving the unprocessed video signals to produce preprocessed video signals; and
    means for electrically connecting, to each other the sensorconverter, the video signal preprocessing means and a driving means for producing preprocessed video signals as output signals from said integrated beam splitter video camera.

8. A beam splitter video camera for use in conjunction with processing an optical iamge from an optical viewing device comprising
   a compact, fluid tight soakable housing including means for defining central area which extends therethrough and means for defining an optical aperture and a viewing opening, each of whic hextend from the exterior of and through said housing into communication with said central area, said housing including means for passing an optical image to be processed from the optical viewing device along a predetermined path through the optical aperture and into the central area;
   means located along said predetermined path, for transmitting a nominal portion of said optical image along a first optical path which extends through the central area and through the viewing opening of said housing and for reflecting the substantial remaining portion of said optical iamge within the central area along a second optical path which includes a portion thereof which is substantially perpendicular to said said first optical path, said transmitting means further including a beam splitter having a beam splitting surface which is coated with a material which, in the visible spectrum, transmits about 5% to about 10% of the optical image along the first optical path and about 80% to about 90% of the optical image along said second optical path, said beam splitter surface being positioned at an angle of 45° relative to the optical path to intercept said optical image;
   means positioned along said first optical path to intercept said nominal portion of said optical image for forming a viewable image of said optical image;
   an optical image processing system positioned within said central area relative to said second optical path to receive and process said remaining substantial portion of said optical image being passed along the second optical path to produce video signals representing said optical image, said optical image processing system including
   a sensor-converter which is responsive to an optical image having an intensity which exceeds a threshold intensity of the sensor-converter, said sensor-converter being positioned within said housing to receive said optical image passing along said second optical path and for converting the optical iamge to unprocessed video electric signals; and
   a lens system positioned between said sensor-converter and said means for focusing onto said sensor-converter, at an intensity level which is at least equal to the threshold intensity level of said converter-sensor, the optical image passing along said second optical path.

9. The video camera of claim 8 wherein said housing includes means for defining a front end portion including a cavity having two ends formed therein wherein the cavity extends along said first optical path and wherein the optical aperture is formed at one end thereof and the viewing opening formed at the other end thereof and in alignment with said optical aperture;
   an elongated central portion having a hollowed-out central area and a rearward portion, said elongated central portion and said rearward portion defining a hollowed-out central area which is substantially perpendicular to and which communicates with the cavity of said first end portion, said elongated central portion enclosing the second optical path and said hollowed-out central area having said sensor-converter and said lens system positioned therein and relative to the second optical path to enable the lens to be adjusted to focus the optical image onto said sensorconverter.

10. The video camera of claim 9 wherein said optical image processing means means includes
   ajdusting means operatively lens system to move the same linearly along the second optical axis relative to the sensorconverter to focus the optical images thereon.

11. The video camera of claim 8 wherein said beam splitting surface is coated with a metal-dielectric material which, in the visible spectrum, transmits about 8% of the optical image along the first optical path and reflects about 72% of the optical iamge along said second optical path.

12. The video camera of claim 11 wherein said optical image receiving means further includes
   a reflecting surface positioned relative to said beam splitter surface for reflecting the remaining substantial portion of said optical image at a selected angle realtive to the first optical path.

13. An integrated beam splitter video camera for use with an endoscope which produces an optical image comprising
   means defining an predetermined path for receiving atone end thereof the optical image from an endoscope and means including a beam splitter for passing a substantial portion of the optical image along an optical path, a portion of which is at a selected angle relative to the predetermined path, said beam splitter further including a beam splitting surface which is coated with a material which, in the visible spectrum, transmits about 8% to about 10% of the optical image along the first optical path and reflects about 70% to about 80% of the optical image along said second optical path, said beam splitter surface being positioned at an angle of about 45° relative to the predetermined path to intercept said optical image;
   means including a solid-state imaging means positioned along said optical path for receiving the optical image passed by said beam splitter along said optical path and for converting the received optical image to video signals; and
   video signal driving means operatively coupled to said solid-state imaging means and positioned remote from the first optical path and the second optical path to avoid intercepting the same, said video signal driving means including means operatively connected to said solid-state imaging means for driving an external output means with said video signals.

14. The integrated beam splitter video camera of claim 13 further comprising
   soakable enclosure means surrounding the optical path defining means, the solid-state imaging means and the video signal driving means and including means for maintaining the same in operative relationship.

15. The integrated beam splitter video camera of claim 13 wherein said beam splitter also passes a nominal portion of said optical image along a first optical path and the remaining substantial portion thereof along a second optical path to the solid-state imaging means and further comprising means positioned along said first optical path to intercept said nominal portion of said optical image for forming a viewable image of said optical image.

16. The integrated beam splitter video camera of claim 15 further comprising
   a lens system positioned between said solid-state imaging means and said beam splitter along the second optical path for focusing the optical image onto said solid-state imaging means.

17. The integrated beam splitter video camera of claim 14 wherien said beam splitting surface which is coated with a material, which in the visible spectrum, transmits about 8% of the optical image along the first optical path and about 72% of the optical image along said second optical path.

18. The integrated beam splitter video camera of claim 14 wherein said means defining the predetermined path further includes
   a reflecting surface positioned relative to said beam splitter surface for reflecting the remaining substantial at a selected angle relative to the first optical path.

19. The integrated beams plitter video camera of claim 18 wherein said selected angle is about 90°.

20. The integrated beam splitter video camera of claim 16 wherein the focal length of such lens system is between about 16 mm. to about 55 mm.

21. The integrated beam splitter video camera of claim 20 wherein the focal length of said lens system is about 27.5 mm.

22. A method for simultaneously producing a viewing image from an optical iamge from an endoscope and for producing video signals representative thereof comprising the steps of
   passing an optical image to be processed from the endoscope along a predetermined path to housing which includes means for defining a central area which extends therethrough;
   receiving within the central area of said hosuing the optical image with an differential transmission/reflecting means located along said predetermined path, for passing a nominal portion of said optical image along a first optical path and for passing the remaining substantial portion of said optical image along a second optical path a portion of which is at a selected angle to said first optcial path wherein said differential transmission/reflecting means further includes a beam splitter having a beam splitting surface which is coated with a material which, in the visible spectrum, transmits about 8% to about 10% of the optical image along the first optical path and reflects about 80% to about 90% of the optical image along said second optical path, said beam splitter surface being positioned at an angle of about 45° relative to the predetermined path to intercept said optical image;
   receiving and processing with an optical iamge processing system within the central area of said housing the remaining substantial portion of said optical image passing along said second optical path for producing video signals representing said optical image.

23. The method of claim 22 further comprising the step of
   intercepting said nominal portion of said optical image along said first optical path and forming a viewable image of said optical image;

24. The method of claim 22 wherein said optical image processing circuit includes a sensor-converter which is responisve to an optical image having an intensity above a threshold intensity level and said sensor-converter is positioned to receive said optical image reflected along said second optical path and further comprising the steps of
   focusing with a lens system located the along the second optical path the optical image onto said converter-sensor.

25. The method of claim 24 further comprising the step of
   converting the optical image to unprocessed video electric signals.

26. The video camera of claim 25 further comprising the steps of
   preprocessing the unprocessed video signals with a video preprocessing circuit means operatively connected to the sensorconverter and located within said housing and remote from the first optical path and the second optical path so as to avoid intercepting the same; and
   transmitting the preprocessed video signals from the video camera to a remote video output circuit.

* * * * *